United States Patent [19]

Lund et al.

[11] Patent Number: 4,791,211

[45] Date of Patent: Dec. 13, 1988

[54] PROCESS FOR THE PRODUCTION OF 2-STILBYLNAPHTHOTRIAZOLE OPTICAL BLEACHES

[75] Inventors: Richard B. Lund, Jackson; Larry W. Bass, Daphne, both of Ala.

[73] Assignee: Ciba-Geigy Corporation, Ardsley, N.Y.

[21] Appl. No.: 5,496

[22] Filed: Jan. 20, 1987

Related U.S. Application Data

[63] Continuation-in-part of Ser. No. 745,822, Jun. 18, 1985, abandoned, which is a continuation of Ser. No. 661,873, Oct. 17, 1984, abandoned, which is a continuation of Ser. No. 424,728, Sep. 27, 1982, abandoned.

[51] Int. Cl.$^4$ ............................................. C07D 249/24
[52] U.S. Cl. .................... 548/260; 534/579; 534/582; 534/689; 548/257
[58] Field of Search ................ 548/257, 261; 534/579, 534/582; 524/91

[56] References Cited

U.S. PATENT DOCUMENTS

| | | | |
|---|---|---|---|
| 2,784,183 | 3/1957 | Keller | 548/260 |
| 4,167,629 | 9/1979 | Fleck | 548/257 |
| 4,219,472 | 8/1980 | Hurter | 534/632 |

*Primary Examiner*—Donald G. Daus
*Assistant Examiner*—Mark W. Noel
*Attorney, Agent, or Firm*—Kevin T. Mansfield; Edward McC. Roberts

[57] ABSTRACT

An improved process for the production of 2-stilbylnaphthotriazole optical bleaches which involves diazotizing aminostilbene 2-sulfonic acids, coupling the thus formed diazonium salt with naphthylamino-sulfonic acid to form the stilbylnaphthyl monoazo salt by adding the naphthylamino-sulfonic acid to the diazonium salt from the diazotization, neutralized to a pH in the range of 6–8, in the presence of 2-butoxyethanol, oxidizing said monoazo salt to form the 2-stilbylnaphthotriazole compounds with air in an aqueous alkaline medium containing butoxyethanol and isolating and recovering said 2-stilbylnaphotriazole optical bleaches as their sodium salts.

4 Claims, No Drawings

PROCESS FOR THE PRODUCTION OF 2-STILBYLNAPHTHOTRIAZOLE OPTICAL BLEACHES

This application is a continuation-in-part of application Ser. No. 745,822, filed on June 18, 1985, abandoned, which is a continuation of application Ser. No. 661,873, filed on Oct. 17, 1984, abandoned, which is a continuation of application Ser. No. 424,728, filed on Sept. 27, 1982, abandoned.

FIELD OF THE INVENTION

This invention relates to a new improved process for preparing 2-stilbylnaphthotriazole optical bleaches and more particularly to the improved procedure for coupling the diazotized aminostilbene with the naphthylamine before cyclization by oxidation.

BACKGROUND OF THE INVENTION

The optical bleaches to which this invention is directed are described in the Keller et al. U.S. Pat. No. 2,784,183, issued Mar. 5, 1957. These compounds fluoresce in the bluegreen range and impart to substances coated or incorporated therewith a bright "white" appearance. The compound: 2-(stilbyl-4″)-(naphtho-1′2′:4,5)-1,2,3-triazole-2″ sulfonic acid sodium salt, as described therein, is a commercial product sold under the trademark "TINOPAL RBS". As such, improvements in manufacturing procedures are of great economic importance.

The general scheme for the synthesis of this compound is according to the reaction scheme of the equations in Table 1.

TABLE I
CHEMISTRY

A. Diazotization

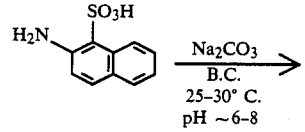

P—Aminostilbene Sulfonic Acid (PASSA)
M.W. 297

Sodium Nitrite
M.W. 69

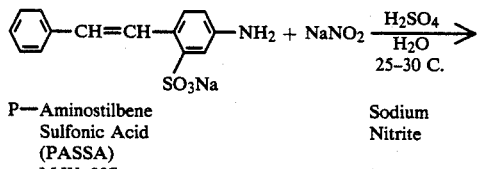

Diazonium Salt
p-Diazostilbenesulfonic Acid Sodium Salt
M.W. 406

B. Coupling

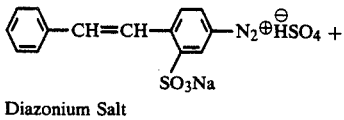

Diazonium Salt

TABLE I-continued
CHEMISTRY

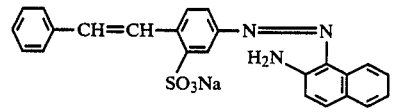

2-Naphthylamine 1-Sulfonic Acid (Tobias acid)
MW 223.2

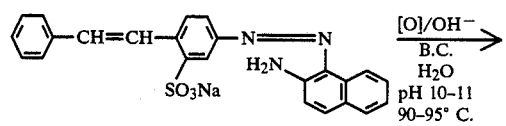

Monoazo Sodium Salt
M.W. 451.5

C. Oxidation

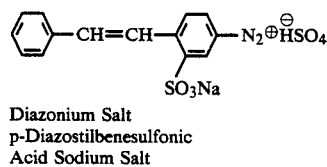

Monoazo Salt $C_4H_9-O-CH_2CH_2-OH$
Butyl Cellosolve (B.C.)

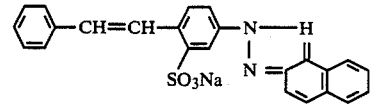

TINOPAL RBS
M.W. 449.5

In the coupling reaction (B) the diazonium salt was neutralized from the acidic diazotizing reaction, cooled to about 10°–15° C. and added to an excess of 2-naphthylamine-1-sulfonic acid (Tobias acid) originally in the presence of lutidine, and recently 2-butoxyethanol, Butyl Cellosolve ($C_4H_9-O-CH_2CH_2OH$). Yields in the range 70–80% based on PASSA were obtained.

Coupling reactions that are reported in the prior art are conducted differently than in the present invention. For example, in Geigy, British No. 781,821 and Keller, U.S. Pat. No. 2,784,183, the diazo compound is added to a neutralized solution of the coupling agent. This mode of addition is the one customarily used for a coupling reaction to avoid decomposition of the diazo compound under basic conditions and is opposite to that employed in the present invention. Crounse, U.S. Pat. No. 3,689,425, also adds the diazo compound to the coupling agent as does Marschall, U.S. Pat. No. 3,157,644. Marschall, however, destroys the excess nitrous acid in the diazo with sulfamic acid before adding it to the coupling agent. Fujita, U.S. Pat. No. 4,263,624, Alder, U.S. Pat. No. 4,141,903 and Fleck, U.S. Pat. No. 4,167,629 also report coupling reactions. Fujita and Alder employ the standard addition of diazo solution to the neutralized coupling agent. Fleck adds the neutralized coupling agent to the diazo solution which is strongly acidic. This is in contrast to the present invention where the diazo solution is neutralized prior to adding the coupling agent to it. In addition to the above disclosures on the coupling process, the use of alcohols including butyl Cellosolve as solvent and the use of sodium acetate or carbonate as neutralization agent are mentioned in these last three references. Only Geigy and Keller refer to the production of 2-stilbylnaphthotriazole compounds. The other references report various other coupling reactions.

THE INVENTION

The present invention is based on the discovery that, in the reaction scheme of Table 1, when the diazonium salt is dissolved in Butyl Cellosolve, neutralized to the pH range 6-8 are coupled by the addition to the solution of the diazonium salt of the stoichiometric amount of Tobias acid, in Butyl Cellosolve (while maintaining the pH), the coupling can take place at or slightly above room temperature (20°-30° C.) and hydrolysis of the diazonium salt is reduced so that the yield, based on PASSA, is increased to about 84-90%.

In addition to the increased yields, energy savings in refrigeration and vessel utilization result. As the Tobias acid is no longer required to excess (10-12%), considerable savings result as this reagent is not inexpensive.

An additional important advantage is the saving of one reaction kettle by adding the Tobias acid coupling agent to the diazonium salt. In this process, the same vessel is used for both the diazotization and the coupling steps. By contrast, two vessels would be required by the usual procedure of forming the diazonium salt (one vessel) and adding it to the neutralized coupling agent (second vessel). Another costly step, destruction of excess nitrous acid after diazotization, is avoided in the present process by neutralizing the diazonium salt to pH 6-8 before adding the Tobias acid. Ordinarily, the nitrous acid would be decomposed by reacting it with sulfamic acid or urea to prevent it from reacting with the coupling agent. This process step, requiring time, labor and materials, is avoided in the present invention while permitting the additional savings of a one kettle process. Overall, the improvements flowing from this invention provide very significant annual savings in the total production.

The process improvements of this invention are not only applicable to the production of TINOPAL RBS but to the other optical bleaches disclosed and described in U.S. Pat. No. 2,784,183 as well as in other couplings of diazonium salts with arylamines and particularly with naphthylamines.

The invention is primarily directed to improvements in the process for preparing 2-stilbylnaphthotriazole optical bleaches which comprises the steps of (a) diazotizing aminostilbene-2-sulfonic acids; (b) coupling the thus formed diazonium salt with naphthylamino sulfonic acid to form the stilbylnaphthyl monoazo salt; (c) oxidizing said monoazo salt to form the 2-stilbylnaphthotriazole compounds; (d) isolating the recovering said 2-stilbylnaphthotriazole optical bleaches as their sodium salts. Specifically, the improvement resides in the step of conducting said coupling (b) by adding the naphthylaminosulfonic acid to the diazonium salt from the diazotization neutralized to a pH in the range of 6-8 in the presence of 2-butoxyethanol ($C_4H_9$—O—$CH_2$—$CH_2$—OH) as solvent for the organic reactants and products.

As set forth below, in its preferred mode, the invention is directed to the preparation of TINOPAL RBS but as mentioned above, it is also applicable to the coupling of diazonium salts with arylamines.

DETAILED DESCRIPTION

In the past the PASSA and sodium nitrite, $NaNO_2$, were dissolved in water and this aqueous combined solution was stored for use at 50° C. This solution together with additional solid $NaNO_2$, as a combined slurry, was charged to the diazotization solution, acidified to less than pH 2. Some Butyl Cellosolve was present as a solvent for the diazonium salt as formed. Upon completion of the diazotization, the reaction mixture was cooled to 10°-15° C. and added over 1-2 hours to another vessel containing a solution of Tobias acid in water and butyl cellosolve. It was then neutralized to pH 6-8 by NaOH or $Na_2CO_3$. The coupling took place in this cool mixture and was complete within 1 hour after the addition.

The resulting monoazo compound, in solution in Butyl Cellosolve, was then rendered alkaline (pH 10-11) and oxidized by air in the presence of a $CuSO_4$ catalyst or by 17% chlorine bleach solution to cyclize the monoazo compound to the triazole compound by ring closure of the adjacent nitrogen atoms at the juncture of the coupled stilbene and naphthyl moieties. This air-oxidation while time consuming affords products with acceptably low coloration after treatment (a) with $Na_2S$ to remove the copper residues and (b) with sodium hydrosulfite (Lykopon) to reduce excessive coloration impurities. The chlorine bleach product is more highly colored and requires further treatment.

The process of this invention utilizes a single vessel for both the diazotization and coupling steps. The $NaNO_2$ (40% solution) and PASSA are introduced separately and concurrently or are premixed and introduced into the vessel. The $NaNO_2$ in the form of its 40% aqueous solution is directly admixed with the PASSA by introduction into the vessel via inline mixer and oval gear metering control of the mixing and feeding into the vessel. Contained in the vessel is a 50% Butyl Cellosolve: 50% water mixture and sufficient acid to maintain the pH below about 2. At higher pH ranges the diazotation is impeded. Tests show that the stated water: Butyl Cellosolve mixture provides the best yields (84%) as compared with Butyl Cellosolve alone (72%) and water alone (78%).

When the diazonium salt completely dissolves in the solvent medium, nearly complete diazotization is obtained. While formic acid is a preferred solvent for this reaction, it is too expensive for use in commercial production.

The time between completion of the diazotization reaction and initiation of the coupling reaction is not critical as long as the holding medium is maintained at pH below about 8. The diazonium salt from PASSA was found to be relatively stable under such conditions even in the presence of a "Metallic Mixture" used to test for stability and suitability for reacting compounds in metal vessels.

Even at 50° C. the diazonium salt, held for 45 hours before initiation of the coupling reaction, did not provide significantly lower yields of the monoazo compound. This diazonium salt is relatively stable as compared to other diazonium compounds.

As mentioned above, the Tobias acid (or the requisite beta-naphthylamines or beta-naphthylamine sulfonic acids) is added to the diazonium salt. While adding the Tobias acid, the reaction mixture is neutralized to pH 6-8 by concurrent addition of aqueous solutions of sodium carbonate or sodium hydroxide. Sodium carbonate is preferred as easier to control despite its tendency to foam. Sodium acetate may also be used.

Care must be taken to keep the pH of this reaction mixture below about 8. Above this critical limit, the stability of the diazonium salt deteriorates rapidly, with lower yield of the monoazo salt.

The rate of addition of the Tobias acid is not at all critical provided that the pH range is within the stated limits. Below pH 6, the rate of coupling is slowed down. Above this range, as mentioned above, the yield is reduced by deterioration of the diazonium compound.

During the addition of the Tobias acid, it is useful to increase the volume of the reaction mixture mix to ensure the solubility of the monoazo compound. Butyl Cellosolve is added in sufficient amount. This may be added before the Tobias acid addition or during this addition. However, it may be preferable to add sufficient Butyl Cellosolve initially before and during the diazo formation as it will remain in the vessel.

The coupling reaction proceeds nicely at about 20°–35° C. when the Tobias acid is added to the diazonium salt in its reaction vessel. The yields of monoazo compound are in the range 78–82% based on the amount of PASSA formerly used. When the old system of adding the diazonium compound to the Tobias acid was used, yields of monoazo compound were drastically reduced unless the reaction mixture was cooled to below 15° C. Even at this low temperature, the yields were 5 to 7% lower than by utilizing the process of this invention.

An additional advantage for the procedure of the present invention is that no excess of Tobias acid is required to ensure optimum yields. A stoichiometric amount of Tobias acid is all that is required. This results in the optimum yields mentioned above. The best yields of the prior art requires the presence of up to about 12% excess of Tobias acid. As Tobias acid is not cheap, such savings are economically important in commercial production.

The rate of addition of Tobias acid and the neutralizing $Na_2CO_3$ is not critical except for the foaming caused by the release of $CO_2$. This can be easily controlled. In batches of about one to two tons of final product diazotized and coupled in a 6000 gal. vessel, the addition of tobias acid and $Na_2CO_3$ was complete in 30 minutes. The reaction may be followed by testing for unreacted diazo salt. This test, at the preferred temperature range of 25°–30° C., is negative in 10–20 minutes. To ensure solubility and completion, the mixture is held for another 30 minutes and then cooled. Before proceeding to the final stage of synthesis, the oxidation, the water soluble impurities are removed by raising the finished monoazo solution to about pH 10 with NaOH, separating and discarding the aqueous layer that forms from the Butyl Cellosolve layer containing the monoazo compound.

The monoazo solution is then diluted by adding water and additional Butyl Cellosolve.

The oxidation and further recovery steps then proceed on this solution of the monoazo compound. This solution is stable and can be stored until needed.

The oxidation is carried out at pH 10 or greater at all times and in the presence of copper sulfate as catalyst (about 25–40 pounds/2000 gal. of monoazo).

The oxidation is achieved by sparging air through the solution at temperatures in the range 75°–100° C., preferably about 90°–92° C. The air is introduced below the surface of the monoazo solution until its characteristic red color is completely gone. This can best be followed by thin layer chromatography. Upon completion of the oxidation the copper is removed by adding $Na_2S$. To remove the pink impurities (not monoazo color) the solution is treated with sodium hydrosulfite (Lycopon). The slurry is then freed of copper sulfide and reduced substances by filtration and the final product is isolated by distillation from its solution containing about 35% Butyl Cellosolve. The final yield via the process of this invention, with its novel procedure for coupling the diazonium salt, is generally in the range 80–82%, about 2 to 10% higher than with the prior art procedures but with additional economies effected by more parsimonious use of Tobias acid and the utilization of less equipment and cooling systems.

The invention will be more completely described in the following examples directed to preferred modes for carrying out the invention. While specific amounts, equipment and reaction condition modifiers, such as pH buffering agents are mentioned, it will be understood that any art recognized equivalents thereof may be judiciously substituted by remain within the intended scope of this invention.

EXAMPLE 1

Laboratory Procedure

Equipment: Two 1-liter three neck flasks with bottom outlet, fitted with stirrer and thermometer. The top flask is equipped with a heating mantle and the bottom flask is cooled with an ice bath.

Procedure: Charge to the upper flask 34.4 g. PASSA 100% (p-aminostilbene sulfonic acid) (0.125 mole) (Assay based on HPLC analysis). Heat to 50°–65° C. with stirring and add $NaNO_2$ 9.5 g. (0.138 mole). Stir at 50°–60° C. and dilute to 190 ml. by adding water if necessary. (23.8 g. of 40% $NaNO_2$ solution could be used instead of solid $NaNO_2$. Final solution volume should be 190 ml.). Charge to the bottom flask 350.0 g. 50% Butyl Cellosolve and 19.3 g. 93% $H_2SO_4$ (0.183 moles). Cool in a water or ice bath to 25°–30° C. Add the amine/nitrite solution from the top flask (through bottom outlet) evenly over 30–45 minutes while maintaining the temperature at 25°–30° C. During addition check with KI starch paper to be sure there is a slight excess of nitrite present and maintain pH 1.5–2.0. Hold for 25°–30° C. for 30 minutes after the addition is complete. The diazo salt solution (568 g., 580 ml) is now ready for the coupling step in the same vessel. Adjust the pH of the diazo salt solution to 5–6 at 25°–30° C. with approximately 10.0 g. $Na_2CO_3$. Add 27.9 g. Tobias acid (0.125 moles) and approximately 16.0 g. $Na_2CO_3$ as required to maintain pH at 6–8. (Total $Na_2CO_3$ charge 26 g.) Addition of Tobias acid and $Na_2CO_3$ takes 5–10 minutes. Stir at 25°–30° C. until diazo spot test is negative (10–20 minutes). Add 50.0 g NaOH 50%, stir for 10 minutes. Stop agitation and let settle for 30 minutes. Separate layers. The remaining upper monoazo layer is now ready to be used in the oxidation step.

Yield: 300 g. of solution containing 48.0 g. of monoazo (as Na salt by HPLC assay), 85% of theory, based on PASSA.

Oxidation: Add to a one liter reactor 314 gm of the monoazo solution, 200 gm of 50% Butyl Cellosolve, 150 gm. water and 2.0 gm of $CuSO_4.5H_2O$. Heat contents to 90° C. and start air sparge. Follow the oxidation by checking monoazo red color. When gone (about 4–5 hours) add 2.0 gm $Na_2S$, 2.0 gms. Lycopon and 4.0 gms.

of filter aid. Stir 15 minutes, filter and wash filter with 100 gm. Butyl Cellosolve and about 400 ml. hot water. Combine filtrate and washes, introduce into steam distillation apparatus and steam distill the Butyl Cellosolve and water from the product TINOPAL RBS, 2-(stilbyl-4")-(naphtho-1',2':4,5)-1,2,3-triazole-2"-sulfonic acid sodium salt.

Yield: 46.5 dry cake: 82.9% based on PASSA.

EXAMPLE 2

Plant Procedure-Diazotization and Coupling Steps

Charge a 6,000 gallon stainless steel reactor with 18.697 lbs. Butyl Cellosolve 50% (2,357 gallons). Start brine cooling and good agitation. Add over 15 minutes 1148 lbs. sulfuric acid 93%. Cool to 25°-30° C. Add simultaneously through an inline mixer over 30 minutes while maintaining 25°-30° C. temperature 2042 lbs PASSA solution as 100% (7.42 moles by HPLC assay, 1334 gallons of 17% weight/weight/aqueous solution at 43.8 gallons/minute rate) and 1410 lbs. $NaNO_2$ 40% aqueous solution (8.17 moles, 130 gallons at 4.4 gallons/minute rate). Hold at 25°-30° C. for 45 minutes.

Coupling: Keep the temperature at 25°-30° C. and adjust the pH to 5–6 by adding approximately 610 lbs. $Na_2CO_3$. Charge 1655 lbs Tobias acid (7.41 moles) and approximately 945 lbs $Na_2CO_3$ as required to maintain the pH at 6–8. Addition should take 30–45 minutes. Watch for foam and slow the addition if necessary. After addition is complete, hold at pH 6–8 until test for unreacted diazo is negative (10–20 minutes) and then hold for another 30 minutes. Cool and rapidly add 2967 lbs. NaOH 50% (238 gallons). Batch will exotherm to 40°–50° C. Stop agitation and allow layers to separate (volume, 4419 gallons) (41,259 pounds). Split off lower aqueous layer (1990 gal.) to the sewer. Add 11,812 lbs water (1415 gallons) as make up, then add as required approximately 10,942 lbs Butyl Cellosolve 50% (1402 gallons) to bring the level to 5246 gallons. Pump this monoazo solution (44,097 pounds, 5246 gallons) to a storage tank. Yield: 44,097 pounds (5246 gallons) of solution containing 2848 pounds of monoazo (as Na salt by HPLC assay), 81% of theory (equivalent to 2702 pounds of TINOPAL RBS).

What is claimed is:

1. In a process for preparing a 2-stilbylnaphthotriazole optical bleach having the steps of:
    (a) diazotizing an aminostilbene 2-sulfonic acid;
    (b) coupling the thus formed diazonium salt with a naphthylamino-sulfonic acid to form a stilbylnaphthyl monoazo salt;
    (c) oxidizing said monoazo salt to form a 2-stilbylnaphthotriazole compound; and
    (d) isolating and recovering said 2-stilbylnaphthotriazole optical bleach as its sodium salt;
the improvement comprising the step of conducting said coupling (b) by adding said naphthylaminosulfonic acid to said diazonium salt from the diazotization, neutralized to a pH in the range of 6–8 and maintaining the pH in the range of 6–8, in the presence of 2-butoxyethanol as a solvent for the organic reactants and products.

2. The process according to claim 1, wherein said optical bleach is 2-(stilbyl-4")-(naphtho-1',2':4,5)-1,2,3-triazole-2-sulfonic acid sodium salt; said aminostilbene-2-sulfonic acid is 4-aminostilbene-2-sulfonic acid which is diazotized and coupled by adding sodium carbonate and 2-naphthylamino-1-sulfonic acid to said diazonium salt.

3. The process according to claim 2, wherein said coupling is carried out by adding said sodium carbonate to the diazonium salt dissolved in the 2-butoxyethanol to the stated pH range and the 2-naphthylamino-1-sulfonic acid is then added in a stoichiometric amount dissolved in 2-butoxyethanol with additional sodium carbonate increments as needed to maintain said pH range.

4. The process according to claim 3, wherein said coupling is conducted at a temperature range of 25°–30° C.

* * * * *